(12) United States Patent
D'Arpiany et al.

(10) Patent No.: US 9,737,289 B2
(45) Date of Patent: Aug. 22, 2017

(54) SINGLE USE, DISPOSABLE, TISSUE SUSPENDER DEVICE

(75) Inventors: Francis D'Arpiany, Vendat (FR); Arnaud Wattiez, Schiltigheim (FR)

(73) Assignee: VECTEC S.A., Hauterive (FR)

( * ) Notice: Subject to any disclaimer, the term of this patent is extended or adjusted under 35 U.S.C. 154(b) by 274 days.

(21) Appl. No.: 13/876,897

(22) PCT Filed: Sep. 29, 2010

(86) PCT No.: PCT/IB2010/002759
§ 371 (c)(1),
(2), (4) Date: Jun. 6, 2013

(87) PCT Pub. No.: WO2012/042290
PCT Pub. Date: Apr. 5, 2012

(65) Prior Publication Data
US 2013/0303856 A1    Nov. 14, 2013

(51) Int. Cl.
*A61B 1/32* (2006.01)
*A61B 17/02* (2006.01)
*A61B 17/04* (2006.01)
*A61D 1/00* (2006.01)
*A61B 17/00* (2006.01)

(52) U.S. Cl.
CPC ...... *A61B 17/0218* (2013.01); *A61B 17/0401* (2013.01); *A61D 1/00* (2013.01); *A61B 2017/00349* (2013.01); *A61B 2017/0417* (2013.01)

(58) Field of Classification Search
CPC . A61B 17/0218; A61B 17/02; A61B 17/3431; A61B 2017/0225; A61F 2/0063; A61F 2/0811; A61F 2/0045; A61F 2/2466; A61F 2/2487; A61F 2002/0068; A61F 2002/0072; A61F 2002/0858; A61F 2220/0016
USPC ........ 606/151; 600/201, 206, 209, 210, 215, 600/217
See application file for complete search history.

(56) References Cited

U.S. PATENT DOCUMENTS 3,835,863 A * 9/1974 Goldberg et al. .............. 604/284
4,657,461 A * 4/1987 Smith .......................... 411/340
(Continued)

FOREIGN PATENT DOCUMENTS

WO    WO9309721    5/1993
WO    WO9408643    4/1994

*Primary Examiner* — Eduardo C Robert
*Assistant Examiner* — Michelle C Eckman
(74) *Attorney, Agent, or Firm* — Hoffmann & Baron, LLP

(57) ABSTRACT

The present invention relates to a single-use, disposable, tissue suspender device comprising a longitudinal body having a distal end and a proximal end, the thickness of the body being substantially constant along a major portion of the length of said body from said proximal end towards said distal end; wherein a region immediately preceding the distal end of the body presents a reduced thickness compared to the remainder of the longitudinal body extending back toward the proximal end; and wherein the distal end comprises a distal bar attached to the region of reduced thickness of the longitudinal body which adopts an unconstrained deviating angle to a longitudinal axis of the longitudinal body. The invention also relates to use of the device for suspending tissue in a human or animal body.

14 Claims, 6 Drawing Sheets

(56) References Cited

U.S. PATENT DOCUMENTS

| | | | |
|---|---|---|---|
| 4,707,906 A * | 11/1987 | Posey | 29/453 |
| 4,741,330 A * | 5/1988 | Hayhurst | 606/144 |
| 5,041,129 A * | 8/1991 | Hayhurst et al. | 606/232 |
| 5,167,627 A | 12/1992 | Clegg et al. | |
| 5,213,575 A * | 5/1993 | Scotti | 604/95.04 |
| 5,226,767 A * | 7/1993 | Foerster, Jr. | 411/340 |
| 5,269,809 A * | 12/1993 | Hayhurst et al. | 606/232 |
| 5,289,817 A * | 3/1994 | Williams et al. | 600/204 |
| 5,370,646 A * | 12/1994 | Reese et al. | 606/324 |
| 5,411,520 A * | 5/1995 | Nash et al. | 606/213 |
| 5,441,042 A * | 8/1995 | Putman | 600/102 |
| 5,531,759 A * | 7/1996 | Kensey et al. | 606/213 |
| 5,545,178 A * | 8/1996 | Kensey et al. | 606/213 |
| 5,601,557 A * | 2/1997 | Hayhurst | 606/232 |
| 5,702,352 A * | 12/1997 | Kimura | A61B 17/0218 600/201 |
| 5,810,884 A * | 9/1998 | Kim | 606/213 |
| 5,861,004 A * | 1/1999 | Kensey et al. | 606/213 |
| 5,873,891 A * | 2/1999 | Sohn | 606/219 |
| 5,879,357 A * | 3/1999 | Heaton et al. | 606/116 |
| 6,068,648 A * | 5/2000 | Cole et al. | 606/232 |
| 6,451,030 B2 * | 9/2002 | Li et al. | 606/139 |
| 6,596,014 B2 * | 7/2003 | Levinson et al. | 606/228 |
| 6,626,919 B1 * | 9/2003 | Swanstrom | 606/153 |
| 6,656,182 B1 * | 12/2003 | Hayhurst | 606/232 |
| 6,692,506 B1 * | 2/2004 | Ory et al. | 606/151 |
| 7,341,558 B2 * | 3/2008 | de la Torre et al. | 600/204 |
| 7,371,245 B2 * | 5/2008 | Evans et al. | 606/151 |
| 7,597,705 B2 * | 10/2009 | Forsberg et al. | 606/213 |
| 7,621,937 B2 * | 11/2009 | Pipenhagen et al. | 606/232 |
| 7,662,161 B2 * | 2/2010 | Briganti et al. | 606/151 |
| 8,118,836 B2 * | 2/2012 | Denham et al. | 606/232 |
| 8,137,364 B2 * | 3/2012 | Zung et al. | 606/144 |
| 8,187,300 B2 * | 5/2012 | Funamura | 606/232 |
| 8,211,122 B2 * | 7/2012 | McIntosh | 606/144 |
| 8,394,113 B2 * | 3/2013 | Wei et al. | 606/151 |
| 8,435,290 B2 * | 5/2013 | Clifford et al. | 623/10 |
| 8,454,655 B2 * | 6/2013 | Yeung et al. | 606/232 |
| 8,480,559 B2 * | 7/2013 | Knapp et al. | 600/37 |
| 8,668,705 B2 * | 3/2014 | Johnston et al. | 606/151 |
| 8,685,059 B2 * | 4/2014 | Walters | 606/213 |
| 8,758,366 B2 * | 6/2014 | McLean et al. | 606/139 |
| 8,758,402 B2 * | 6/2014 | Jenson et al. | 606/213 |
| 8,771,260 B2 * | 7/2014 | Conlon et al. | 606/1 |
| 8,790,356 B2 * | 7/2014 | Darois et al. | 606/144 |
| 8,827,891 B2 * | 9/2014 | Roberts | 600/37 |
| 8,834,492 B2 * | 9/2014 | McLean et al. | 606/139 |
| 8,961,540 B2 * | 2/2015 | Baker et al. | 606/139 |
| 2002/0128684 A1 * | 9/2002 | Foerster | A61B 17/0401 606/232 |
| 2004/0037669 A1 * | 2/2004 | Bauer | 411/523 |
| 2004/0097974 A1 * | 5/2004 | De Leval | 606/144 |
| 2004/0243178 A1 * | 12/2004 | Haut et al. | 606/232 |
| 2005/0004575 A1 * | 1/2005 | Sgro et al. | 606/72 |
| 2005/0187565 A1 * | 8/2005 | Baker et al. | 606/151 |
| 2005/0187567 A1 * | 8/2005 | Baker et al. | 606/151 |
| 2005/0216040 A1 * | 9/2005 | Gertner et al. | 606/151 |
| 2006/0009792 A1 * | 1/2006 | Baker et al. | 606/151 |
| 2006/0142784 A1 * | 6/2006 | Kontos | 606/139 |
| 2006/0167481 A1 * | 7/2006 | Baker et al. | 606/151 |
| 2006/0235446 A1 * | 10/2006 | Godin | 606/151 |
| 2006/0253132 A1 * | 11/2006 | Evans et al. | 606/151 |
| 2007/0049929 A1 * | 3/2007 | Catanese et al. | 606/46 |
| 2007/0073316 A1 * | 3/2007 | Sgro et al. | 606/151 |
| 2007/0112385 A1 * | 5/2007 | Conlon | 606/232 |
| 2007/0142846 A1 * | 6/2007 | Catanese et al. | 606/142 |
| 2007/0276412 A1 * | 11/2007 | Catanese et al. | 606/143 |
| 2007/0277815 A1 * | 12/2007 | Ravikumar | A61B 90/57 128/99.1 |
| 2007/0293879 A1 * | 12/2007 | Baker et al. | 606/151 |
| 2008/0039874 A1 * | 2/2008 | Catanese et al. | 606/142 |
| 2008/0071297 A1 * | 3/2008 | Kohl et al. | 606/151 |
| 2008/0195145 A1 * | 8/2008 | Bonutti et al. | 606/207 |
| 2008/0277853 A1 * | 11/2008 | Menn | 269/87 |
| 2009/0222029 A1 * | 9/2009 | Gordin et al. | 606/151 |
| 2010/0010448 A1 * | 1/2010 | Deckard | 604/174 |
| 2010/0076462 A1 * | 3/2010 | Bakos et al. | 606/146 |
| 2010/0081875 A1 * | 4/2010 | Fowler et al. | 600/114 |
| 2010/0094094 A1 | 4/2010 | DeSantis et al. | |
| 2010/0211097 A1 * | 8/2010 | Hadba | A61B 17/06166 606/232 |
| 2011/0029012 A1 * | 2/2011 | Tegels | 606/213 |
| 2011/0040312 A1 * | 2/2011 | Lamson et al. | 606/151 |
| 2011/0054492 A1 * | 3/2011 | Clark | 606/139 |
| 2011/0082472 A1 * | 4/2011 | Harris et al. | 606/139 |
| 2011/0125189 A1 * | 5/2011 | Stoll et al. | 606/232 |
| 2012/0078057 A1 * | 3/2012 | Scott | 600/201 |
| 2012/0191124 A1 * | 7/2012 | Brister et al. | 606/192 |
| 2012/0203223 A1 * | 8/2012 | Terry et al. | 606/42 |
| 2012/0245598 A1 * | 9/2012 | Brown et al. | 606/139 |
| 2013/0012966 A1 * | 1/2013 | Park et al. | 606/151 |
| 2013/0061857 A1 * | 3/2013 | McNally et al. | 128/852 |
| 2013/0090672 A1 * | 4/2013 | Butler et al. | 606/151 |
| 2013/0317521 A1 * | 11/2013 | Choi et al. | 606/130 |
| 2014/0222030 A1 * | 8/2014 | Devries et al. | 606/139 |
| 2014/0371537 A1 * | 12/2014 | Marczyk et al. | 600/204 |
| 2015/0012006 A1 * | 1/2015 | Hausen et al. | 606/108 |
| 2015/0025553 A1 * | 1/2015 | Del Nido et al. | 606/151 |
| 2015/0087914 A1 * | 3/2015 | Navis | 600/204 |
| 2015/0088133 A1 * | 3/2015 | Minskoff et al. | 606/49 |
| 2015/0088170 A1 * | 3/2015 | Baker et al. | 606/151 |

\* cited by examiner

SINGLE USE, DISPOSABLE, TISSUE SUSPENDER DEVICE

This application claims priority based on an International Application filed under the Patent Cooperation Treaty, PCT/IB2010/002759, filed Sep. 29, 2010.

BACKGROUND OF THE INVENTION

The present invention relates to medical devices used in surgery, and in particular to tissue retainer or suspender devices adapted to suspend or retain human or animal tissue, for the duration of the surgical intervention, inspection, observation or operation, in a position determined by the operator of the device, whilst leaving the operator's hands free thereafter for other tasks.

Single use, disposable medical devices have become popular over the years with the advancing progress made in non-invasive or minimally invasive surgical techniques, such as in keyhole surgery, for example laparoscopy or celioscopy based surgical techniques. Additionally, widespread implementation of these single use devices has enabled not only a reduction in the costs of the devices, and treatment as a whole, for example because post-use resterilisation is no longer needed, but also has opened up the possibility for some of the materials used to be recovered in recycling programs.

One of the problems with non-invasive, or minimally invasive surgery is that the constraints of operating, observing or inspecting through one or several small insertions in the body often makes it necessary to reach parts of the body which lie under other body tissue, for example, under organs, muscle layers, cartilage, and the like. Naturally, one could always attempt to approach the target part of the body via a more direct route, by moving the human or animal body into a suitable position before or during surgery, but this is often inconvenient and may not provide the ideal environment in which to carry out the intervention, or may even be counter-productive to the aims of reducing trauma in general. Even in open surgery, there are also situations where tissue, organs or other body parts are required to be held, retained or suspended, temporarily from the field of intervention. With open surgery, for example, it is fairly commonplace to use surgical clamps. Such clamps, however, have several drawbacks: they are often unwieldy, or voluminous, making them unsuitable for working in small spaces or cavities, and because of their clamping effect, they often crush the tissue to which they are attached, potentially creating a further source of trauma to that part of the body. Additionally, if the clamps are made of surgical steel, then they will require resterilisation after the intervention has finished, with all the inherent costs involved therein.

SUMMARY OF THE INVENTION

The present invention proposes to solve the disadvantages of known tissue retaining or suspending devices by proposing a single-use, disposable, suspender device adapted to suspend or retain, for the duration of the surgical intervention or operation, human or animal tissue, and thereafter be withdrawn and disposed of appropriately in accordance with standard medical procedures for disposable single-use devices in general. The suspender device according to the present invention has been found to be particularly useful where bodily constraints, for example, such as the abdominal cavity, force the practitioner to work within a confined space, replete with overlapping tissue structures, when approaching the intervention from the non-invasive or minimally invasive perspective. The suspender device of the present invention can furthermore be integrated into a kit providing a means to introduce said suspender device into the body tissue to be suspended, and a locking means enabling the device to be optionally locked off at a given position in accordance with the desires of the operator.

Accordingly, the single-use, disposable tissue suspender device of the present invention comprises:

a longitudinal body having a distal end and a proximal end, the thickness of the body being substantially constant along a major portion of the length of said body from said proximal end towards said distal end;

wherein a region immediately preceding the distal end of the body presents a reduced thickness compared to the remainder of the longitudinal body extending back toward the proximal end; and wherein the distal end comprises a distal bar attached to the region of reduced thickness of the longitudinal body which adopts an unconstrained deviating angle to a longitudinal axis of the longitudinal body.

Other objects according to the invention will become self-apparent as the invention is described in more detail hereafter, but the applicant also envisages a method for suspending human or animal tissue, using the device according to the present invention.

Preferably, the distal bar comprises a body, the thickness of which is substantially the same as that of the longitudinal body of the device.

It is, however, even more preferred that the distal bar comprise a body having a first and a second section of differing thicknesses, the first section of the body of the distal bar being substantially the same as that of the longitudinal body, and the second section of the body of the distal bar being approximately half as thick as that of the first section. To this end, it is particularly preferred that the second section of the body of the distal bar extend from the first section of the body of the distal bar.

Insofar as thicknesses of the longitudinal body of the device are concerned, the applicant has discovered that it is preferable to use longitudinal body thicknesses in the range of between about 0.9 mm and 2.1 mm, and that it is particularly advantageous to use suspender devices having longitudinal body thicknesses of about 1.6 mm. The reasons for this are that if the longitudinal body has a thickness below about 0.9 mm, it becomes difficult to provide a suspender device which is sufficiently mechanically resistant to carry out the suspending function of the tissue, since other parts of the device have even smaller thicknesses, and in particular, the distal bar of the device. Additionally, if the longitudinal body thickness is above about 2.1 mm, the puncture wound inflicted by the device or the incision necessary to insert it would require post-intervention suturing of the suspended tissue or the skin through which the device is inserted. However, by staying within the thickness ranges given, it is possible to suspend tissue without having to suture said tissue or skin through which the device had entered after the intervention. This represents a major saving in time and effort for the operator of the intervention, and also greatly reduces patient discomfort and trauma.

The region immediately preceding the distal end of the body having a reduced thickness compared to the remainder of the longitudinal body which extends back toward the proximal end can be obtained in several different ways. For example, the reduced thickness can be the result a constant gradual and equal tapering of the material of the longitudinal body located about the longitudinal axis of the longitudinal body. Alternatively, and most preferably, the reduced thickness region can be obtained by providing a shoulder, the proximal end of which has the same thickness as the longitudinal body, and which then gradually diminishes in thickness in a distal direction towards an attaching section as described hereafter. Irrespective of the particular shape of the region of reduced thickness the corresponding reduction can be either stepped or smooth, but is preferably smooth.

Preferably, the attaching section extends from the longitudinal body to the first section of the body of the distal bar. It also preferably has an unconstrained radius of curvature comprised between about 0 degrees and 150 degrees. The curvature that is imposed on the attaching section is a function of the material used in the various parts of the device and the mechanical constraints that are transmitted through the crystalline structure of the material, especially when a particularly preferred polymer material is used for the various parts of the device, such as polypropylene polymers. By carefully selecting said material, it is possible to impose a constraint that will cause the attaching section to curve naturally into an unconstrained position, and since the distal bar is attached to the attaching section, said bar naturally assumes an unconstrained position that is an angle which deviates from the longitudinal axis of the longitudinal body of the device. In a most preferred embodiment of the present invention, the unconstrained deviating angle of the distal bar is comprised between 0 degrees and 150 degrees in relation to the axis of the longitudinal body.

It is also to be noted that according to still yet another preferred embodiment, the first section and second section of the body of the distal bar are at different unconstrained angles with respect to the longitudinal body. In such an unconstrained conformation, the distal bar adopts an "anchor-like" shape, which is particularly suited for suspending tissue when engaged therewith.

The distal bar as mentioned above is preferably attached to the longitudinal body via an attaching section of material of substantially equivalent thickness to that of the second section of the body of the distal bar, or of substantially equivalent thickness to the region of reduced thickness of the longitudinal body. Even more preferably, the length for which the second section extends from the first section of the body of the distal bar is substantially equal to the length of the region of reduced thickness of the longitudinal body minus the length of the attaching section.

According to one preferred embodiment, the longitudinal body and distal bar are both made of the same material, and the attaching section made of a different material. Alternatively, the longitudinal body and attaching section can both be preferably made of the same material, and the distal bar made of a different material. In yet another preferred alternative, the longitudinal body is made of a first material, and the attaching section and distal bar are both made of the same but different material to the longitudinal body. In still yet another preferred alternative embodiment, the longitudinal body, attaching section, and distal bar, are each made of a different material to the others. However, in a most preferred embodiment according to the invention, the longitudinal body, attaching section, and distal bar are all made of the same material. This material is preferably high density polypropylene copolymer. Even more preferably, the device is made of moulded high density polypropylene copolymer.

Turning now to the proximal end of the tissue suspender device, the latter also comprises a constrained prehensile tail describing a radius of curvature comprised between 0 degrees and 180 degrees, attached to the longitudinal body. This prehensile tail preferably imparts mechanical constraint through the crystalline structure of the material of the device along the longitudinal axis of the longitudinal body towards the distal bar at the distal end of the body.

In yet a further preferred embodiment of the present device, it further comprises visible device positioning markers located along the longitudinal body at predetermined spaced apart intervals. The objective of these positioning markers is to facilitate use by the operator of the device, so that the latter knows when to stop inserting the device into introduction means to be described hereafter, and subsequently, the limit at which to stop inserting the device into the body whilst being safe in the knowledge that the distal end of the device will deploy itself correctly.

In addition to what has been described thus far, the device can also further comprise locking means to lock off the tissue suspender device at a predetermined position, wherein the locking means surround and engage the longitudinal body of the suspender device at its proximal end, for example, in the region of the prehensile tail.

In view of the relative thickness of the longitudinal body of the suspender device, the locking means is preferably a removable clip that engages frictionally and elastically with said longitudinal body of the suspender device. Preferably, said clip can be placed at, or adjacent to, the most proximal of the positioning markers. In general, the clip will rest against the skin on the outside of the body, with the remainder of the device, including the longitudinal body and distal bar, having traversed the skin and entered the body to pierce and bear against target tissue. The weight of the target tissue, or other biological structure against which the device bears or abuts, the elastic recoil thereof and the effects of gravity, all influence to a certain extent the final position of the locking means, and the operator will adjust the position thereof along the longitudinal body in accordance with these factors, the desired position of the tissue to be suspended, retained or held, and the desire to minimize trauma to the suspended tissue due to the tension applied or the position thereof with respect to other parts of the body.

As mentioned above, the device also preferably further comprises tissue introduction means surrounding the suspender device. In the present specification, the expression "tissue introduction means" does not refer to means for introducing tissue into the body, but rather means adapted to facilitate the introduction of the suspender device into the body and into target tissue. Consequently, it is therefore preferred that the tissue introduction means according to the present invention comprise a cannula comprising a bevelled cutting distal end edge and a proximal end housing, and the device being inserted into the introduction means via the proximal end housing of said tissue introduction means. In this configuration, the distal end of the suspender device is constrained within the cannula in substantially longitudinal alignment with said cannula until release of the device into the body, i.e. until the introduction means has pierced or passed through the target tissue and the suspender device can be activated or released on the other side thereof. The bevelled cutting distal edge of the introduction means is responsible for piercing the skin, and traversing or piercing the target tissue to be suspended. Such introduction means are useful when the device is made out of relatively flexible polymeric material, but for example, would not be necessary if the device were made from a more rigid material, such as surgical grade steel or wire, and which is completely within the realms of possibility of the present invention.

As mentioned above, the first, or distal, positioning marker on the longitudinal body of the tissue suspender device is used to indicate to the operator where to stop inserting the tissue suspender device into the introduction means. Thus, it is preferred that the first, or distal, positioning marker be aligned with the proximal end of the introduction means. In practice, this generally means that the tissue suspender device is inserted into the introduction means until the first, distal marker is in alignment with the proximal end of the housing of the introduction means. The second, or proximal, positioning marker is used to indicate to the operator the minimum distance of insertion that the tissue suspender device has to be pushed to in order for the distal bar to deploy itself fully outside of the introduction means once the latter have been introduced into the body. In a manner similar to that used for insertion of the suspender device into the introduction means, this involves pushing the tissue suspender device through the introduction means so that the proximal end of the housing of the introduction means is aligned with the second, proximal, positioning marker. The operator can of course push the tissue suspender device through the introduction means further than the alignment of the proximal end of the housing with the second, proximal marker, but it is preferred for the second positional, and proximal, marker to be aligned with the proximal end of said housing.

Accordingly, the present invention also envisages a method for suspending tissue of a human or animal body, comprising:

introducing a tissue suspender device as described in the present application into and through a target tissue to be suspended;

activating the tissue suspender device such that the distal bar of said device adopts an unconstrained deviating angle with respect to the longitudinal axis of the body of said device;

exerting traction on the proximal end of said suspender device to engage the bar onto the target tissue and pull said tissue away from its natural position.

Preferably, the method also further comprises the step of applying locking means to the suspender device to lock off said device at a predetermined position, thereby leaving the operator of the device free to carry out other operations.

As explained above, a preferred embodiment of the present method also further comprises the step of introducing the suspender device into the introduction means before introduction of the device into and through a target tissue, whereby the introduction means are pushed through the body and target tissue, the distal bar of the suspender device is activated by pushing thereof through the introduction means, thereby freeing the distal bar upon exit from the distal extremity of the introduction means, and allowing the distal bar to adopt an unconstrained deviant angle in comparison to the longitudinal axis of the longitudinal body of the suspender device.

BRIEF DESCRIPTION OF THE DRAWINGS

The device and method of the present invention will now be described in more detail, with reference to an example and the accompanying drawings, given for illustrative purposes, in which.

EXAMPLE OF A DEVICE ACCORDING TO THE INVENTION

Figure 1:
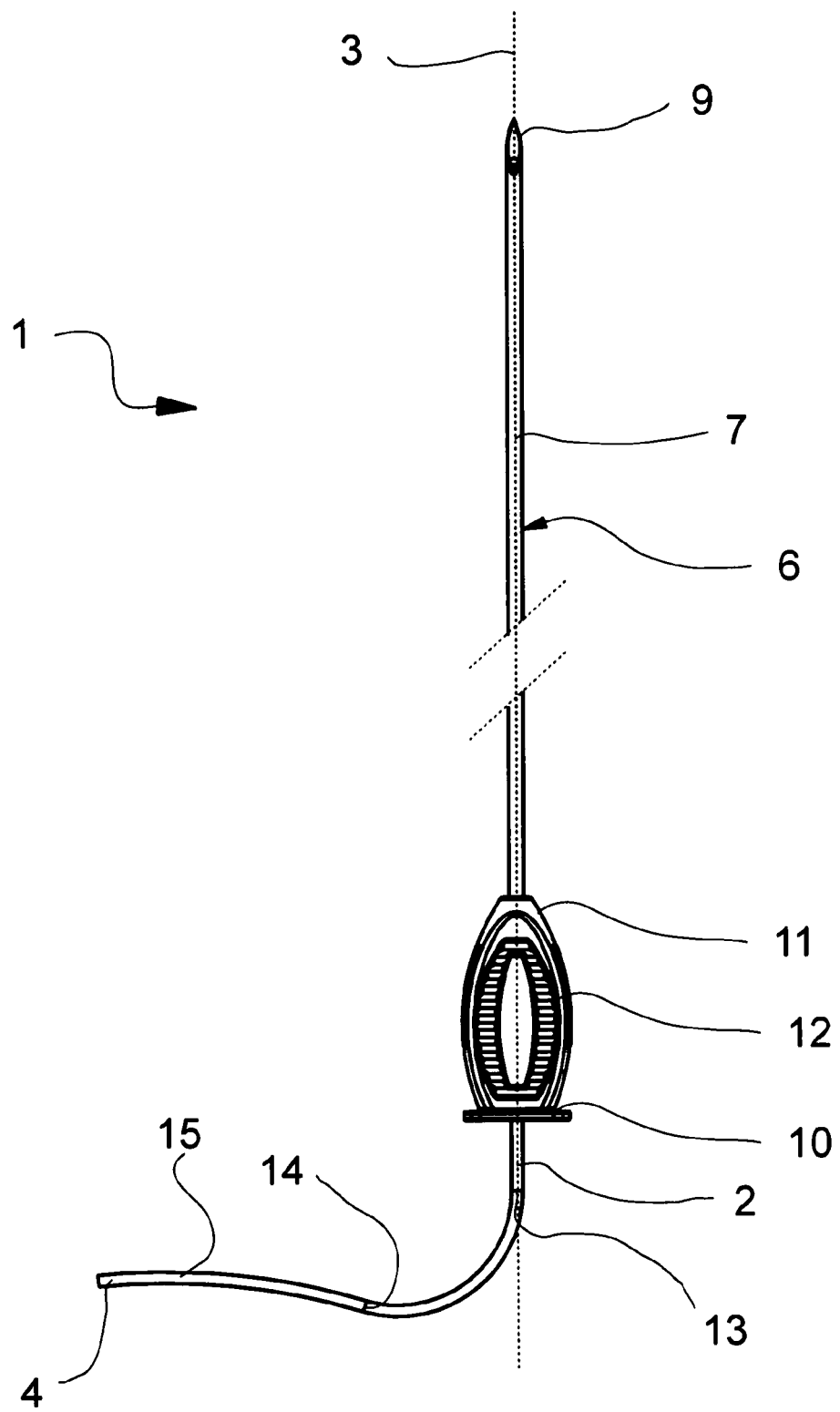
FIG. 1 is a schematic representation of a tissue suspender device according to the present invention inserted into the device's introduction means.

A tissue suspender device referenced generally by the reference number 1, and according to the invention, is illustrated by FIGS. 1 to 4. In FIG. 1, the suspender device is shown to comprise a longitudinal body 2, having a longitudinal axis 3, a proximal end 4 similar to a tail, and a distal end, which is out of sight in FIG. 1 for reasons that will be explained hereafter. The suspender device has been introduced into introduction means, referenced generally by the reference number 6, and comprising a cannula 7 having a distal extremity 8 with a sharpened, bevelled edge 9 adapted to cutting or piercing through human or animal body tissue. At its proximal end 10, the introduction means 6 has a polymer material housing body 11, provided with ribbing 12 to supply a gripping surface for the operator. The proximal end 4 of the tissue suspender device 1 is provided with positioning markers 13, 14. Marker 13 indicates the position at which insertion of the device into the introduction means should stop before introduction into the body to avoid the distal end of the tissue suspender device from deploying itself before it is required. Marker 14 indicates the position representing the minimum limit of introduction of the tissue suspender device into the body. The two markers 13, 14 are positioned in a predetermined manner along the length of the longitudinal body in an area designated prehensile tail 15, since this is the area used to push the suspender device through the introduction means by hand. The markers 13, 14 are spaced apart from each other according to the required length of the tissue suspender device. Useful lengths of tissue suspender devices according to the invention have been found to be in the range of 200 mm to 300 mm. The prehensile tail 15 has an arcuate shape with a radius of curvature comprised between about 0 degrees and about 180 degrees. The applicant has found that, by choosing a suitable material for at least the longitudinal body 2 of the device, of which the prehensile tail 15 is a part, it is possible to impart a mechanical constraint along the longitudinal body to the distal end of the tissue suspender device. This mechanical constraint is caused by the particular crystalline properties of the material chosen to make up the tissue suspender device. As mentioned elsewhere, the applicant has discovered that a particularly suitable material is a high density polypropylene polymer with nucleation, exhibiting an excellent balance of stiffness with low temperature toughness, and made under the reference Purell EP 274P by the company LyondellBasell Industries, in the Netherlands.

Figure 2:
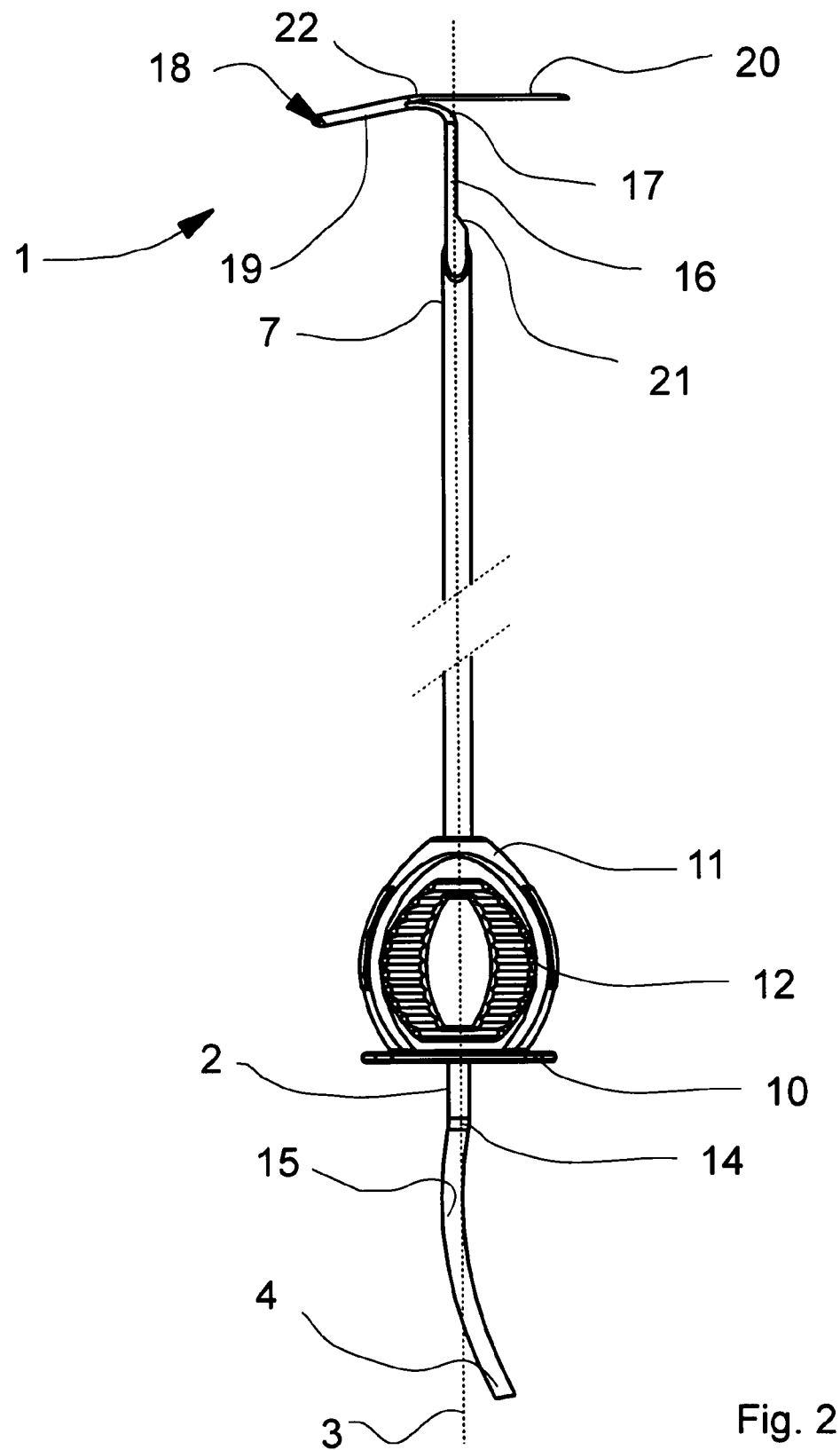
FIG. 2 is a similar representation to that of FIG. 1, in which the tissue suspender device has been inserted to beyond the distal end of the introduction means and the distal bar attached via attaching section of the longitudinal body is now visible in an unconstrained form.
Figure 3:
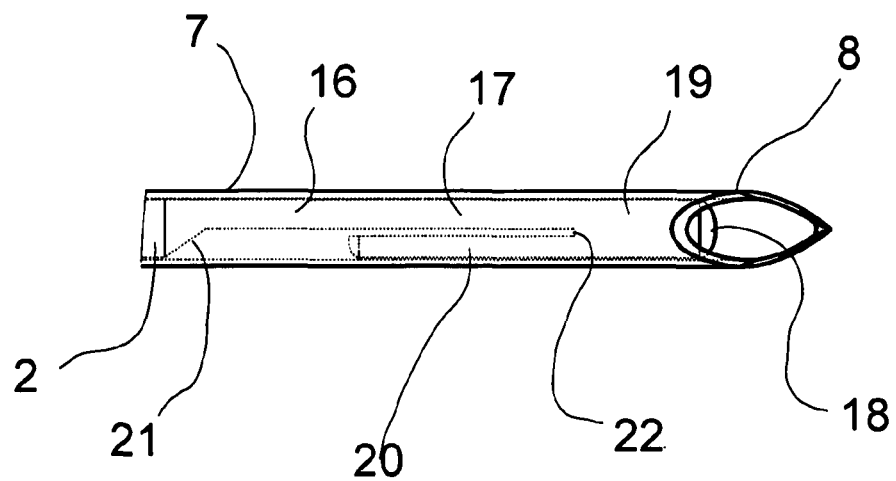
FIG. 3 is a magnified view of the distal end of the introduction means into which the tissue suspender device has been inserted, the tissue suspender being outlined in dashed lines and in a constrained form.
Figure 4:
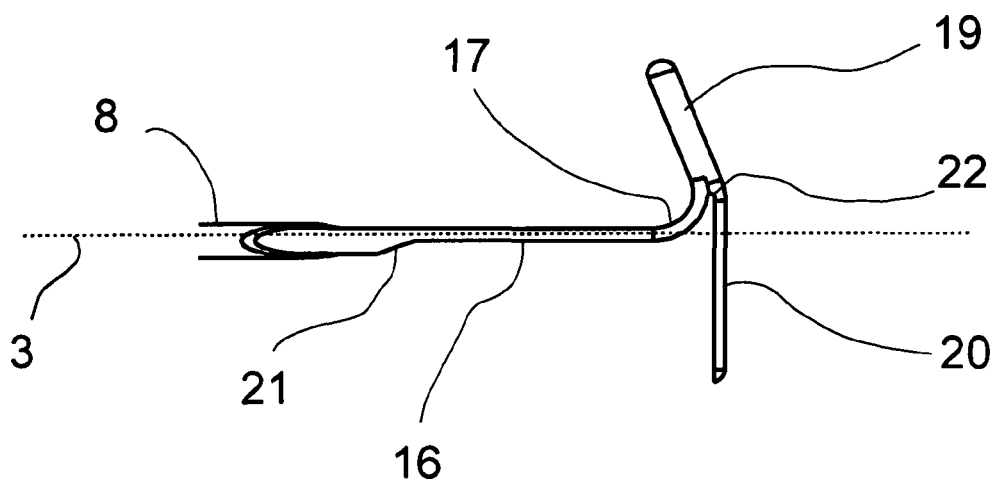
FIG. 4 is a similar magnified view of the distal end of the introduction means and the tissue suspender device, but this time with the distal bar of the suspender device now visible and in an unconstrained form outside of the introduction means.

Turning now to FIG. 2, the distal part of the longitudinal body 2 can be seen. It should be noted that the thickness of the body 2 along the longitudinal axis 3 is substantially constant along a major portion of the length of said body from said proximal end 4 towards said distal end. In particular, it is preferred that the thickness of the body be comprised between about 0.9 mm and 2.1 mm, with a particular preference for a thickness of the longitudinal body set to 1.6 mm. FIG. 2 also shows the region of reduced thickness 16, an attaching section 17, and the distal bar 18 having two distinct sections of different thicknesses, i.e. a first section 19, and a second section 20, all of which have become visible after having been pushed out of the distal end 8 of the introduction means 6. As can be seen from FIG. 2, the distal bar adopts an unconstrained form that causes it to deviate from the longitudinal axis 3 by an angle comprised between 0 degrees and 150 degrees. This unconstrained form is a result of the constraint imposed by the prehensile tail 15 and the choice of material used to make up the longitudinal body 2 of the tissue suspender.

Insofar as the region of reduced thickness 16 is concerned, this is obtained by splitting part of the longitudinal body 2 in the distal region of the suspender device along the longitudinal axis 3. The split starts off at a shoulder 21 which reduces smoothly and gradually in the distal direction to a thickness approximately half that of the initial body thickness. The region 16 of reduced thickness then leads to the attaching section 17, which has a radius of curvature comprised between about 0 degrees and about 150 degrees. The attaching section 17 connects to the distal bar at attachment point 22, which attachment point forms an acute angle with the second section 20 of the distal bar 18. The first section 19 of the distal bar 18 has a thickness which is substantially the same as that of the longitudinal body 2, and the second section 20 of the distal bar 18 being has a thickness which is approximately half as thick as that of the first section 19. Additionally, the second section 20 of the distal bar 18 extends from the first section 19 of the body of the distal bar, and the length for which the second section 20 extends from the first section 19 of the distal bar 18 is substantially equal to the length of the region of reduced thickness, including the shoulder, of the longitudinal body 2 minus the length of the attaching section 17. In this way, and as can be seen from the magnified view in FIG. 3, the second section 20 of the distal bar 18 can be pushed back towards the region of reduced thickness, thereby constraining the attaching section 17 and first section 19 of the distal bar 18 into a constrained position which will allow insertion into the cannula of the introduction means 6 via the proximal end 10 thereof. As can be seen from FIG. 4, the distal bar 18 adopts when freed of the introduction means, an unconstrained form which deviates from the longitudinal axis by an angle comprised between about 0 degrees and about 150 degrees. One can see however that the second section 20 extends in a substantially perpendicular direction to said longitudinal axis 3.

Figure 5:
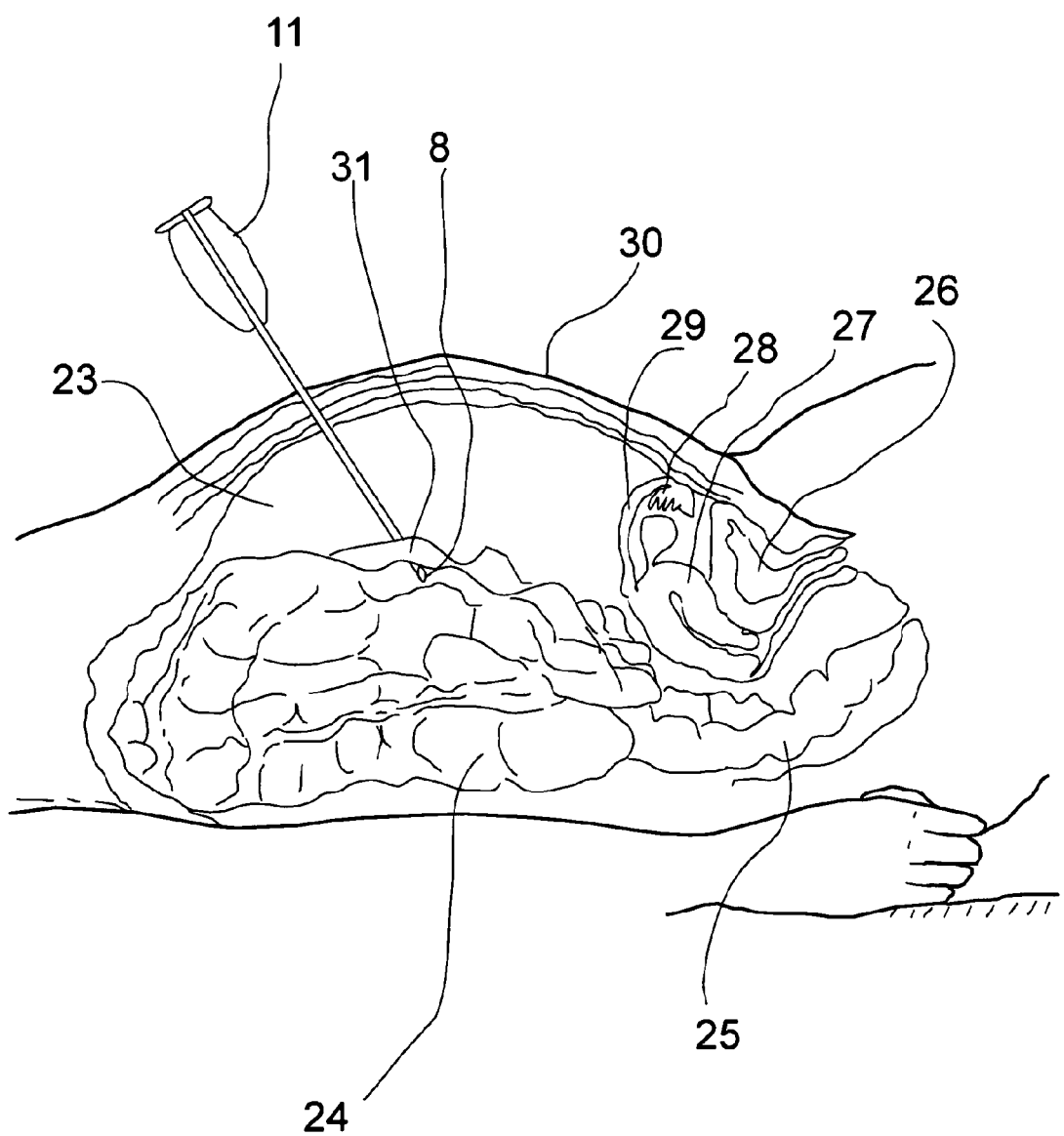
FIG. 5 is a schematic representation of a partial transection of the abdominal cavity of a female human, showing insertion of the introduction means into a target tissue.
Figure 6:
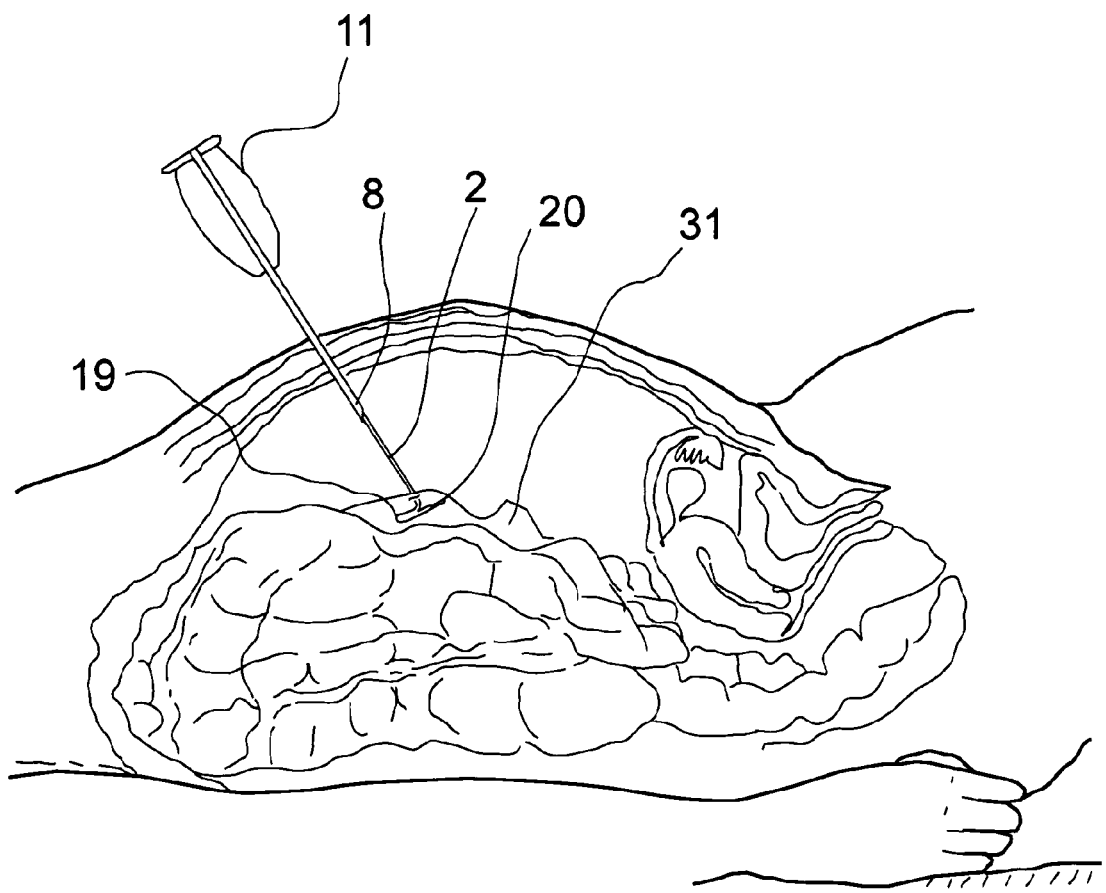
FIG. 6 is a similar representation to FIG. 5, with the difference that the suspender device has been deployed, noticeable from the unconstrained form of the distal bar, after having been inserted through one side of the target tissue and released the other side.
Figure 7:
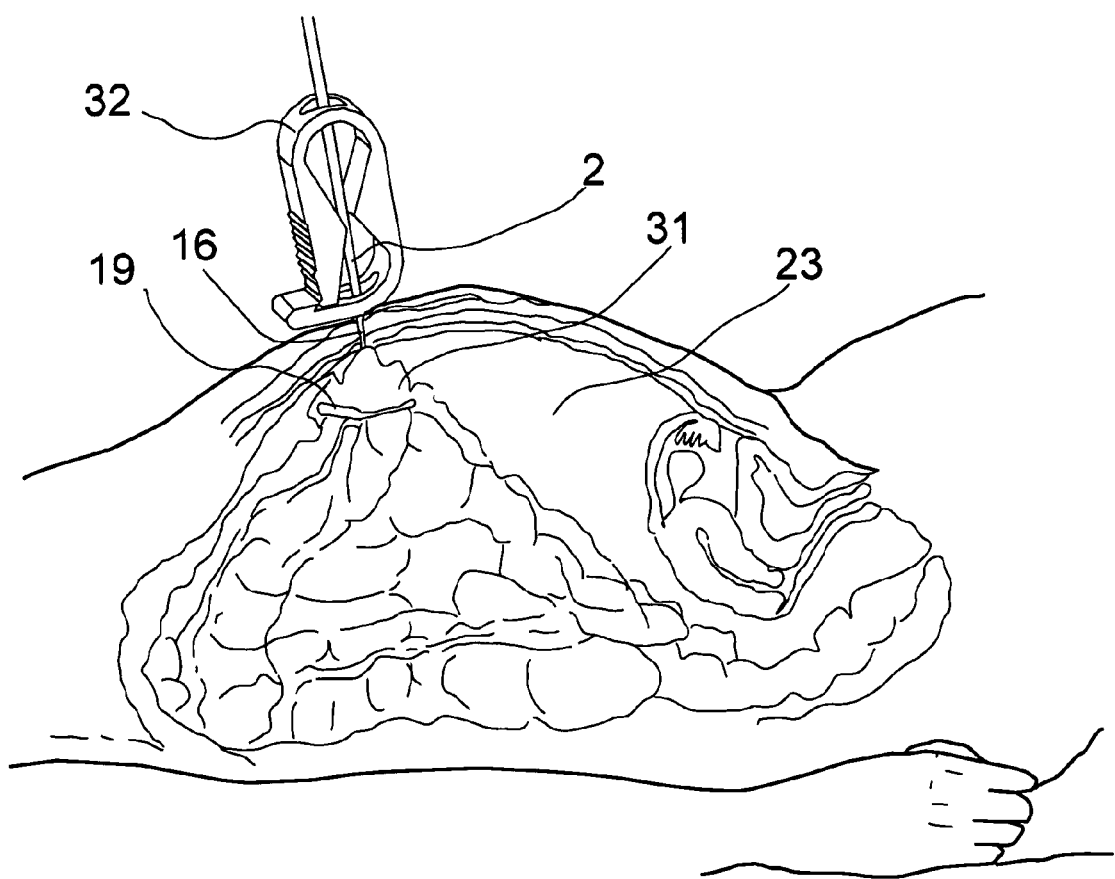
FIG. 7 is yet another similar representation to FIGS. 5 and 6, in which the suspender device has been locked off with a clamp in a position determined by the operator along the longitudinal body of the suspender device, thereby exerting a suspending or retaining force on the tissues held by the suspender device of the invention.

Moving on now to FIGS. 5 to 7, these figures depict the method of use of the tissue suspender device according to the present invention. FIGS. 5 to 7 represent a partly sectional view of the abdominal cavity 23 of a human female. Also depicted are the intestines 24, 25, the bladder 26, the uterus 27, an ovary 28 and a fallopian tube 29. The wall of the abdomen is indicated by 30. In typical laparoscopic or coelioscopic procedures, gas is insufflated into the abdominal space in order to provide a volume in which to work, handle the instruments, and see the various organs and tissue structures. In this particular example, the tissue suspender device is going to be used to suspend the intestines in a position away from the adjacent reproductive organs in order to allow better access to said organs without unduly traumatising the patient. Thus, the introduction means 6, into which the suspender device 1 has previously been inserted to the first marker position 13, are inserted through the abdominal wall 30 into the abdominal cavity 23. The introduction means 6, via the bevelled cutting edge 8 of the cannula 7, can easily puncture the skin and muscle wall and enter the abdominal cavity 23. Other entry points, as are common for coelioscopic or laparoscopic interventions are not shown, but can be used to assist the operator in this manipulation, for example, with trocars through which a camera and pincers have been inserted. The target tissue 31 is located and held in preparation for piercing by the introduction means, and the introduction means then inserted therethrough. In FIGS. 5 to 7, the target tissue 31 is adipose tissue that envelopes the intestinal tract 24, 25. As the puncture wound created by the introduction means 6, and the suspension device 1, remains small, of the order of 1 mm, the wound heals without recourse to sutures of the structures affected.

Subsequently, as illustrated in FIG. 6, the suspender device 1 is pushed out of the cannula 7 into the abdominal cavity 23, having traversed the target tissue 31. As the distal bar 18 of the suspender device 1 is pushed out the bar is activated, or released from, its constrained form that it had adopted while inserted into the introduction means 6. Consequently, the distal bar 18, and its two sections 19 and 20, adopt an angled configuration which deviates from the longitudinal axis 3 of the longitudinal body 2 of the suspender device 1. The introduction means 6 are then withdrawn, leaving the suspender device 1 in place, the length of which is sufficient to exceed the distance to the abdominal wall and thereby remain seizable by the operator.

Finally, in FIG. 7, one can see that the tissue suspender device has been retracted slightly, causing the distal bar 18 to bear upon, abut against, and engage the target tissue 31 as the device 1 is withdrawn upwards. Once an appropriate position has been reached with which the operator is satisfied, the operator can apply the locking mechanism to the longitudinal body 2 of the device 1 and lock-off the device in that position, thereby freeing up the abdominal cavity 23 for further intervention. In the present example, the locking means is a sliding clamp 32 similar to those used in dialysis for clamping tubes, and which can elastically engage the longitudinal body 2 by friction.

After use, when the tissue suspender is no longer needed, for example at the end of the intervention, it can be removed by cutting the longitudinal body at its region of reduced thickness, thereby separating the longitudinal body from the distal bar. The distal bar can then be removed through a trocar in an appropriate manner, and the remainder of the longitudinal body of the device withdrawn out of the tissue through which it had been inserted, and out of the body via the introduction site in the abdominal wall.

Further modifications and changes to the invention described herein will be apparent to the skilled person and are considered to the extent possible, to fall within the spirit and scope of the present invention.

The invention claimed is:

1. A single-use, disposable, tissue suspender device comprising:
   a longitudinal body defined by a longitudinal axis and having a distal end and a proximal end, the thickness of the body being substantially constant along a major portion of the length of said body from said proximal end towards said distal end, and the longitudinal body including visible device positioning markers located along the longitudinal body at predetermined spaced apart intervals;
   a constrained prehensile tail disposed at the proximal end of the longitudinal body, the tail being capable of achieving an unconstrained radius of curvature between 0 degrees and 180 degrees;
   a section of reduced thickness extending from and integrally attached to said distal end of said longitudinal body, said section of reduced thickness having a thickness less than the thickness of the longitudinal body;
   a curved attachment section extending from and integrally attached to a distal end of said section of reduced thickness; and
   a distal bar integrally attached to a distal end of said curved attachment section at an attachment point, said distal bar having a first section and a second section extending in opposite directions from said attachment point such that said second section forms an acute angle with said attachment section in an unconfined state, said first section extending from said attachment point at a first unconstrained angle with respect to said longitudinal axis of said longitudinal body and said second section extending from said attachment point at a second unconstrained angle with respect to said longitudinal axis of said longitudinal body, said first unconstrained angle being different than said second unconstrained angle such that said distal bar forms an anchor shape,
   wherein the thickness of the longitudinal body is between about 0.9 mm to about 2.1 mm, and
   wherein the longitudinal body, the attaching section, and the distal bar are all made of the same molded high density polypropylene copolymer material, and
   wherein the tail imparts mechanical constraint through the crystalline structure of the material of the device along the longitudinal axis of the longitudinal body towards the distal bar at the distal end of the body.

2. A single-use, disposable, tissue suspender device according to claim 1, wherein the section of reduced thickness comprises a constant gradual and equal tapering portion of the longitudinal body located about the longitudinal axis of the longitudinal body.

3. A single-use, disposable, tissue suspender device according to claim 1, wherein the section of reduced thickness comprises a shoulder, the proximal end of which has the same thickness as the longitudinal body, and which then gradually diminishes in thickness in a distal direction.

4. A single-use, disposable, tissue suspender device according to claim 1, wherein the distal bar comprises a body, the thickness of which is substantially the same as that of the longitudinal body.

5. A single-use, disposable, tissue suspender device according to claim 1, wherein the first section and the second section of the distal bar have differing thicknesses, the first section of the the distal bar being substantially the same as that of the longitudinal body, and the second section of the distal bar being approximately half as thick as that of the first section.

6. A single-use, disposable, tissue suspender device according to claim 5, wherein the curved attachment section has a substantially equivalent thickness to that of the second section of the distal bar, or of substantially equivalent thickness to the section of reduced thickness of the longitudinal body, and said curved attachment section has an unconstrained radius of curvature comprised between about 0 degrees and 150 degrees.

7. A single-use, disposable, tissue suspender device according to claim 5, wherein the attaching section extends from the longitudinal body to the first section of the body of the distal bar.

8. A single-use, disposable, tissue suspender device according to claim 1, wherein the length for which the second section extends from the attachment point of the distal bar is substantially equal to the length of the section of reduced thickness of the longitudinal body minus the length of the curved attachment section.

9. A single-use, disposable, tissue suspender device according to claim 1, further comprising a lock to lock off the tissue suspender device at a predetermined position, wherein the lock surrounds and engages the longitudinal body of the suspender device at its proximal end.

10. A single-use, disposable, tissue suspender device according to claim 1, wherein the lock is a removable clip that engages frictionally and elastically with the longitudinal body of the suspender device.

11. A single-use, disposable, tissue suspender device according to claim 1, further comprising a cannula surrounding the suspender device, the cannula comprising a beveled cutting distal end edge and a proximal end housing, and the device is inserted therein via the proximal end housing of the cannula, with the distal end of the suspender device being constrained within the cannula in substantially longitudinal alignment until release of the device into the body.

12. A method for suspending tissue of a human or animal body, comprising:
   introducing a tissue suspender device according to claim 1 into and through a target tissue to be suspended;
   activating the tissue suspender device such that the distal bar of said device adopts an unconstrained deviating angle with respect to the longitudinal axis of the body of said device;
   exerting traction on the proximal end of said suspender device to engage the bar onto the target tissue and pull said tissue away from its natural position.

13. A method according to claim 12, further comprising applying a lock to the suspender device to lock off said device at a predetermined position.

14. A method according to claim 12, further comprising introduction of the suspender device into a cannula before introduction of the device into and through a target tissue, whereby the cannula is pushed through the body and target tissue, the distal bar of the suspender device is activated by pushing thereof through the cannula, thereby freeing the distal bar allowing it to adopt an unconstrained deviant angle in comparison to the longitudinal axis of the longitudinal body of the suspender device.

* * * * *